(12) United States Patent
Boughanem

(10) Patent No.: US 10,206,790 B2
(45) Date of Patent: Feb. 19, 2019

(54) SHOULDER REPLACEMENT/ARTHROPLASTY GLENOID PROSTHESIS COMPRESSION DEVICE

(71) Applicant: Jamal Boughanem, Hilo, HI (US)

(72) Inventor: Jamal Boughanem, Hilo, HI (US)

(*) Notice: Subject to any disclaimer, the term of this patent is extended or adjusted under 35 U.S.C. 154(b) by 162 days.

(21) Appl. No.: 15/380,627

(22) Filed: Dec. 15, 2016

(65) Prior Publication Data

US 2018/0168825 A1    Jun. 21, 2018

(51) Int. Cl.
*A61F 2/46* (2006.01)

(52) U.S. Cl.
CPC .... *A61F 2/4612* (2013.01); *A61F 2002/4622* (2013.01); *A61F 2002/4624* (2013.01); *A61F 2002/4628* (2013.01); *A61F 2002/4631* (2013.01)

(58) Field of Classification Search
CPC . A61B 17/808; A61B 17/8872; A61F 2/4081; A61F 2002/4085; A61F 2/46; A61F 2/4603; A61F 2/4612; A61F 2002/4622; A61F 2002/4631; A61F 2002/4679
See application file for complete search history.

(56) References Cited

U.S. PATENT DOCUMENTS

| 5,578,032 | A  | * | 11/1996 | Lalonde | A61B 17/282 606/205 |
| 6,579,296 | B1 | * | 6/2003  | Macey   | A61B 17/808 606/86 R |
| 7,326,212 | B2 | * | 2/2008  | Huebner | A61B 17/1728 606/328 |
| 8,080,045 | B2 | * | 12/2011 | Wotton, III | A61B 17/8866 606/324 |
| 2015/0100080 | A1 | * | 4/2015  | Kohler | A61B 17/8866 606/205 |

* cited by examiner

*Primary Examiner* — Christopher Beccia
(74) *Attorney, Agent, or Firm* — Plager Schack LLP; Mark H. Plager; Kara Verryt

(57) ABSTRACT

A device for compressing a glenoid prosthesis against a scapula bone while cement is drying during a shoulder replacement surgery may include a compression arm pivotally attached to a grab arm; a compression pad attached to a first end of the compression arm; and a grabbing structure attached to a first end of the grab arm, wherein the first end of the compression arm is aligned with the first end of the grab arm such that the grabbing structure extends from the grab arm past the compression pad to releasably engage with a shoulder bone.

5 Claims, 4 Drawing Sheets

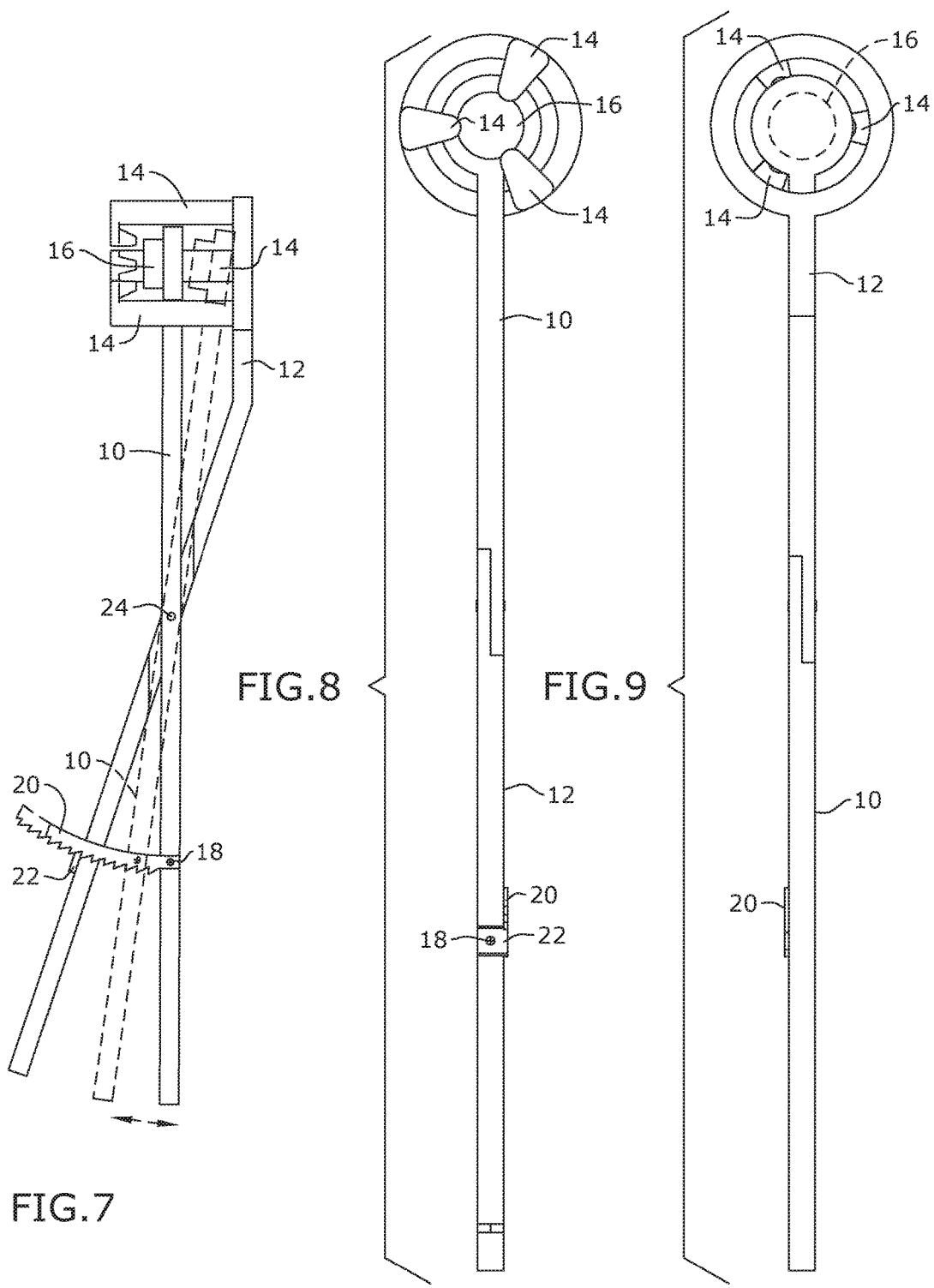

SHOULDER REPLACEMENT/ARTHROPLASTY GLENOID PROSTHESIS COMPRESSION DEVICE

BACKGROUND

The embodiments herein relate generally to medical devices, and more particularly, to a compression device for shoulder replacement procedures.

During a standard total shoulder replacement, a surgeon resurfaces the socket part of the joint (i.e., the glenoid part of the scapula) by reaming, drilling holes, and compressing prosthesis after cement application. The prosthesis is manually held down and compressed against bone while the cement dries, which can take about 10-13 minutes. Manual finger compression is suboptimal for this process, because the pressure applied is variable and inconsistent and can lead to the glenoid component loosening, which is a major cause of later failure of the shoulder replacement.

Devices exist to compress prosthesis to bone in knee replacement (for patellar component compression while the cement dries). However, these devices are not suitable for compressing the glenoid component during shoulder replacement surgery.

Therefore, what is needed is a device to mechanically compress the glenoid prosthesis against the bone while the cement dries during a shoulder replacement.

SUMMARY

Some embodiments of the present disclosure include a device for compressing a glenoid prosthesis against a scapula bone while cement is drying during a shoulder replacement surgery. The device may include a compression arm pivotally attached to a grab arm; a compression pad attached to a first end of the compression arm; and a grabbing structure attached to a first end of the grab arm, wherein the first end of the compression arm is aligned with the first end of the grab arm such that the grabbing structure extends from the grab arm past the compression pad to releasably engage with a shoulder bone. In embodiments, the grabbing structure may grab the shoulder bone(s) while the compression pad places compressive force on the glenoid prosthesis while the cement is drying.

BRIEF DESCRIPTION OF THE FIGURES

The detailed description of some embodiments of the invention is made below with reference to the accompanying figures, wherein like numerals represent corresponding parts of the figures.

FIG. 7 is a left side view of one embodiment of the present disclosure.

FIG. 8 is a back view of one embodiment of the present disclosure.

FIG. 9 is a front view of one embodiment of the present disclosure.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to mechanically compress the glenoid bone while the cement is drying during a shoulder replacement and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Compression Arm
2. Compression Pad
3. Prongs
4. Grab Arm
5. Hinge
6. Latch Lock The various elements of the device of the present disclosure may be related in the following exemplary fashion. It is not intended to limit the scope or nature of the relationships between the various elements and the following examples are presented as illustrative examples only.

Figure 1:
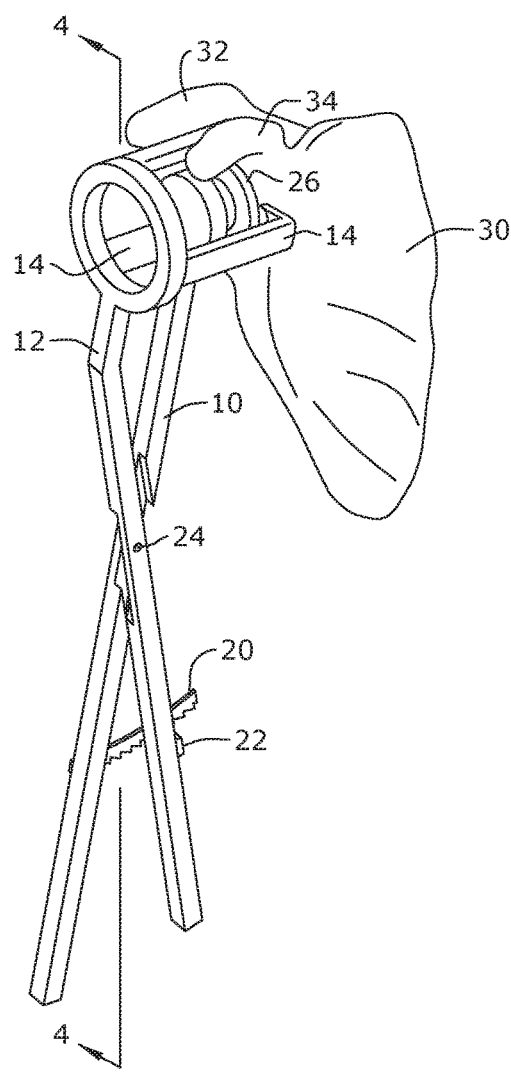
FIG. 1 is a perspective view of one embodiment of the present disclosure, shown in use.
Figure 2:
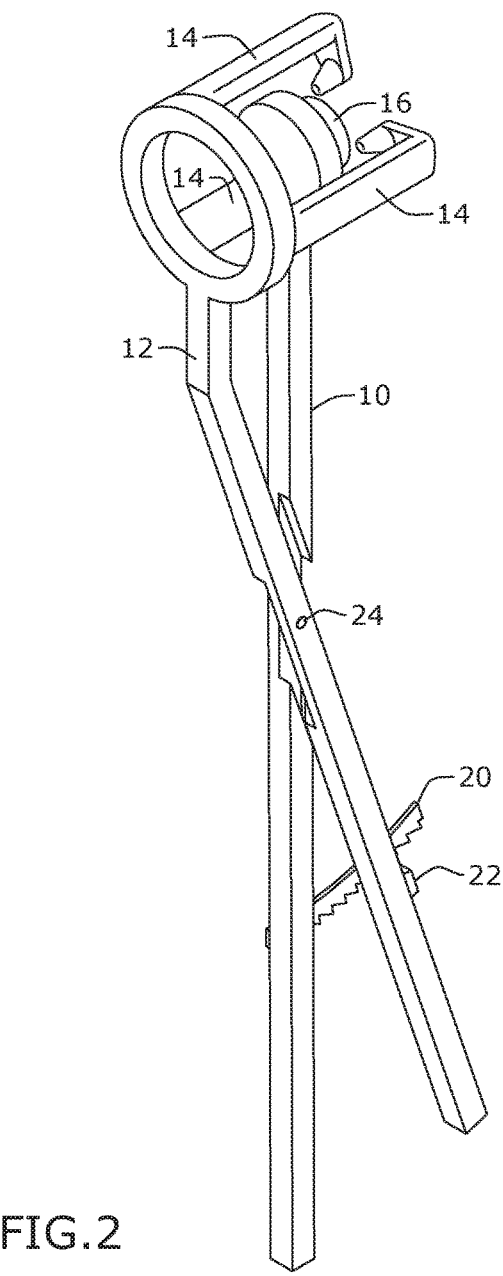
FIG. 2 is a perspective view of one embodiment of the present disclosure.
Figure 3:
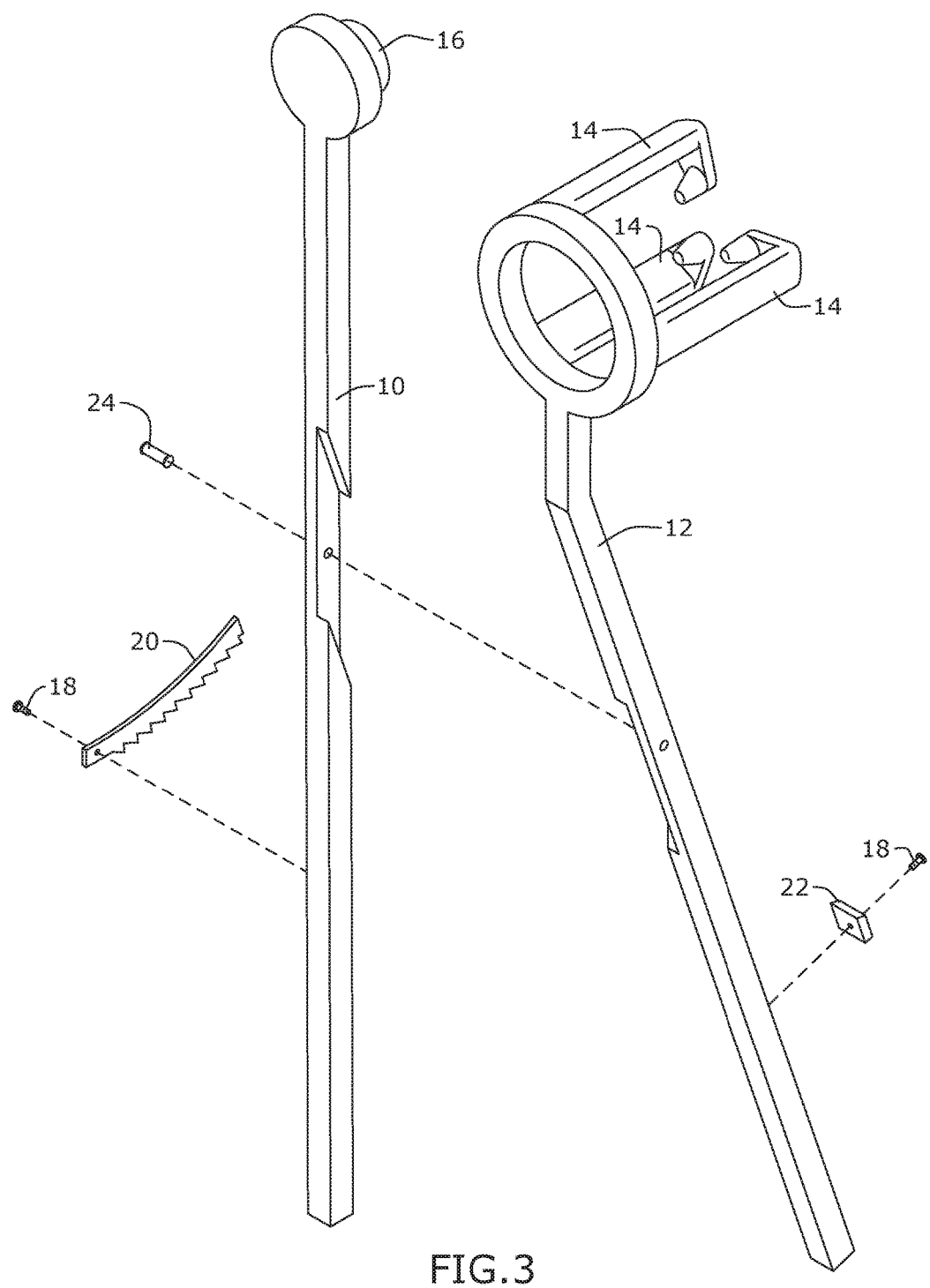
FIG. 3 is an exploded view of one embodiment of the present disclosure.
Figure 4:
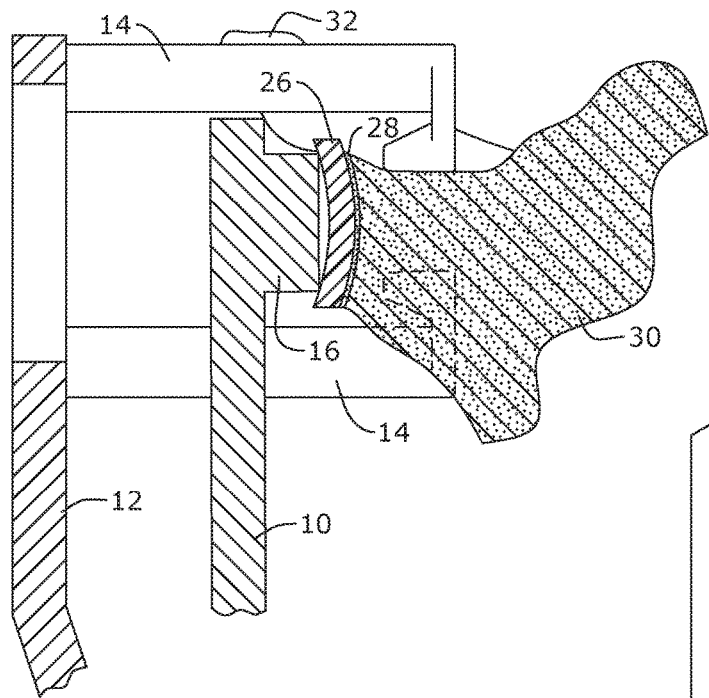
FIG. 4 is a section view of one embodiment of the present disclosure, taken along line 4-4 in FIG. 1.
Figure 6:
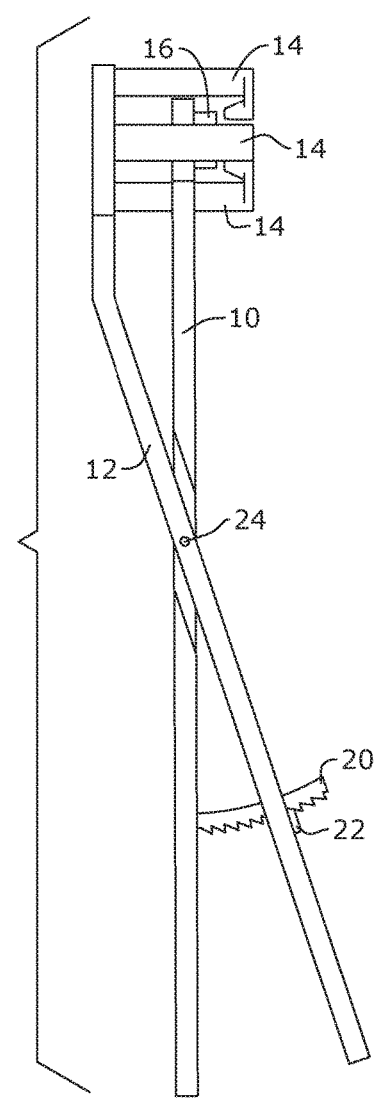
FIG. 6 is a right side view of one embodiment of the present disclosure.
Figure 5:
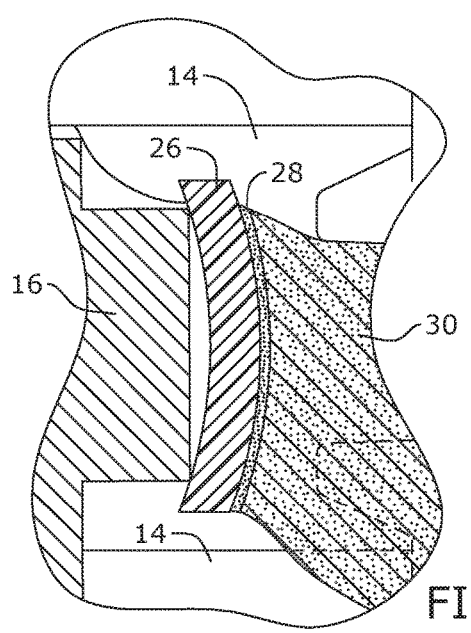
FIG. 5 is an enlarged section view of one embodiment of the present disclosure.

By way of example, and referring to FIGS. 1-9, some embodiments of the present disclosure include a device for compressing a glenoid prosthesis 26 against a scapula bone 30 while cement 28 is drying during a shoulder replacement surgery, the device comprising a compression arm 10 pivotally attached to a grab arm 12, such that the compression arm 10 and the grab arm 12 interact in a scissor-like function; a compression pad 16 attached to a first end of the compression arm 10; and a grabbing structure attached to a first end of the grab arm 12, wherein the first end of the compression arm 10 is aligned with the first end of the grab arm 12, such that the grabbing structure extends from the grab arm 12 past the compression pad 16 to grab onto a shoulder bone, such as the scapula 30, the acromion bone 32, and/or the coracoid bone 34. When in use, the grabbing structure may engage with the shoulder bones in a way to put pressure back toward the compression pad 16, while the compression pad 16 aligns with and puts pressure on a glenoid prosthesis 26 aligned with the scapula 30. Thus, the device of the present disclosure put compressive pressure on the glenoid prosthesis 26 while, for example, the cement 28 between the scapula 30 and the glenoid prosthesis 26 cures.

As shown in the Figures, the compression arm 10 and the grab arm 12 may be attached to one another via a hinge pin 24 positioned at, for example, a substantially central location along the length of each of the compression arm 10 and the grab arm 12. The positioning of the compression arm 10 with respect to the grab arm 12 may be fixed using a lock, such as a latch lock 20. In some embodiments, one of the compression arm 10 and the grab arm 12 may comprise the latch lock 20, while the other of the compression arm 10 and the grab arm 12 may comprise a lock edge 22 configured to engage with the latch lock 20, such that the two arms 10, 12 are secured in a fixed position relative to one another. The latch lock 20 and the lock edge 22 may be attached to the compression arm 10 and grab arm 12 using any suitable fastener, such as screws 18. Fixing the position of the compression arm 10 and the grab arm 12 may provide for consistent compressive pressure being placed on the glenoid prosthesis 26 during use of the device. While the Figures show the use of a latch lock 20, any locking or securing device may be used. The locking or securing device may be positioned at any area along the length of the compression arm 10 and the grab arm 12 and, in some embodiments, is positioned distal from the grabbing structure and compression pad 16.

In embodiments, the grabbing structure may comprise any structure suitable for grabbing onto the shoulder bones. In a first example, the grabbing structure may comprise a plurality of prongs 14, such as three evenly spaced prongs 14, extending from the first end of the grab arm 12. As shown in the Figures, the first end of the grab arm 12 may comprise a ring having a diameter larger than that of the compression pad 16. The prongs 14 may extend outward from the ring at about, for example, a 90° angle. Ends of the prongs 14 distal from the ring may bend inwards toward the center of the ring, such that the prongs 14 have a lipped end that may grab onto the shoulder bones.

Alternatively, the grabbing structure may comprise screw holes such that the first end of the grab arm 12 may be removably attached to the shoulder bones using a plurality of screws.

As shown in the Figures, the compression pad 16 may be attached to the first end of the compression arm 10. The compression pad 16 may have any desired size or shape and, in some embodiments, is circular with a diameter less than that of the grabbing structure.

The device of the present disclosure may be made of any suitable or desired materials. In embodiments, the compression arm 10 and the grab arm 12 may be made of a rigid material, while the compression pad 16 may comprise a less rigid or soft material.

To use the device of the present disclosure, the surgeon would prepare the glenoid for the cemented glenoid prosthesis 26, which could be, for example, a high molecular weight polyethylene or pegged or keeled glenoid prosthesis. The surgeon may then add the cement 28, apply the glenoid prosthesis 26, and use the device to compress the prosthesis 26 against the bone, such as the scapula 30, while the cement 28 dries. The grabbing structure may removably engage with the bone, while the compression pad 16 may place compressive force onto the prosthesis 26. The force may be kept constant by locking the arms into place using, for example, the latch lock 20.

The device of the present disclosure may provide mechanical compression of the glenoid prosthesis 26 against the scapula bone 30 while the cement 28 dries, thus providing for improved surgical technique. The device may also obviate the need for applying manual compression, while simultaneously making the pressure utilized more consistent, uniform, and measurable. Improving cement technique during this step of the surgery may improve survival rates of the shoulder replacement surgery.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A device for compressing a glenoid prosthesis against a scapula bone while cement is drying during a shoulder replacement surgery, the device comprising:
    a compression arm pivotally attached to a grab arm;
    a compression pad attached to a first end of the compression arm; and
    a grabbing structure attached to a first end of the grab arm, wherein the first end of the compression arm is aligned with the first end of the grab arm such that the grabbing structure extends from the grab arm past the compression pad to releasably engage with a shoulder bone, wherein:
        the grabbing structure comprises a plurality of prongs extending from the first end of the grab arm; and
        the first end of the grab arm comprises a ring having a diameter larger than a size of the compression pad.

2. The device of claim 1, wherein each of the plurality of prongs extends outward from the ring at a 90° angle.

3. The device of claim 1, wherein ends of the prongs distal from the ring bend inwards toward a center of the ring, such that each of the prongs has a lipped end designed to grab onto the shoulder bone.

4. The device of claim 1, wherein the compression arm and the grab arm are attached to one another via a hinge pin positioned at a substantially central location along a length of each of the compression arm and the grab arm.

5. The device of claim 1, wherein:
    the compression arm has a latch lock extending therefrom;
    the grab arm has a lock edge attached thereto; and
    the latch lock is designed to engage with the lock edge to releasably secure the compression arm in a desired position with respect to the grab arm.

* * * * *